(12) United States Patent
Wolleben et al.

(10) Patent No.: US 10,996,179 B2
(45) Date of Patent: May 4, 2021

(54) SYSTEM AND METHOD TO DETECT GROUND MOISTURE

(71) Applicant: Skaha Remote Sensing Ltd., Naramata (CA)

(72) Inventors: Maik Wolleben, Naramata (CA); Heinz Wolleben, Langenhagen (DE)

( * ) Notice: Subject to any disclaimer, the term of this patent is extended or adjusted under 35 U.S.C. 154(b) by 3 days.

(21) Appl. No.: 16/298,979

(22) Filed: Mar. 11, 2019

(65) Prior Publication Data
US 2020/0292472 A1    Sep. 17, 2020

(51) Int. Cl.
| | |
|---|---|
| *G01N 22/04* | (2006.01) |
| *G01S 19/13* | (2010.01) |
| *G01N 33/24* | (2006.01) |
| *G01V 1/00* | (2006.01) |
| *G01V 3/06* | (2006.01) |
| *G01V 3/08* | (2006.01) |

(Continued)

(52) U.S. Cl.
CPC .......... *G01N 22/04* (2013.01); *G01N 33/246* (2013.01); *G01R 29/0878* (2013.01); *G01S 19/13* (2013.01); *G01V 1/008* (2013.01); *G01V 3/06* (2013.01); *G01V 3/08* (2013.01); *G01V 3/12* (2013.01)

(58) Field of Classification Search
CPC . G01V 1/008; G01V 3/08; G01V 3/12; G01V 3/06; G01R 29/0878
USPC ........................................................ 324/344
See application file for complete search history.

(56) References Cited

U.S. PATENT DOCUMENTS

| | | | | |
|---|---|---|---|---|
| 3,639,834 A | * | 2/1972 | Walker | .................. G01N 22/04 |
| | | | | 324/637 |
| 3,803,570 A | * | 4/1974 | Barlow | ................ G01N 27/223 |
| | | | | 318/643 |

(Continued)

FOREIGN PATENT DOCUMENTS

| | | |
|---|---|---|
| CA | 2916617 | 2/2007 |
| CN | 1847832 | 10/2006 |

(Continued)

OTHER PUBLICATIONS

Thomas Schmugge, Soil Moisture Sensing with Microwave Radiometers, Purdue Univerity Pudue e-Pubs LARS Symposia paper 392, http://docs.lib.purdue.edu/lars_symp/392, 1980, 10 p (Year: 1980).*

(Continued)

*Primary Examiner* — Clayton E. LaBalle
*Assistant Examiner* — Kevin C Butler
(74) *Attorney, Agent, or Firm* — Richard D. Okimaw

(57) ABSTRACT

A system for measuring moisture in soil below the ground surface comprises at least one passive microwave sensor device configured to measure natural thermal emissions from the soil and output a data signal and a processing circuit operably coupled to the at least one passive microwave sensor wherein the processing circuit is configured to receive the data signal and compile a soil moisture profile. The system further comprises a wide-band antenna wherein the at least one passive microwave sensor is located therein and an elongate horizontal mounting frame extending between first and second ends wherein the first end is securable to a mobile agricultural device and wherein the wide-band antenna is secured to the second end so as to position the wide-band antenna at a distance above the ground surface.

14 Claims, 5 Drawing Sheets

(51) Int. Cl.
  *G01V 3/12* (2006.01)
  *G01R 29/08* (2006.01)

(56) References Cited

U.S. PATENT DOCUMENTS

| | | | | |
|---|---|---|---|---|
| 3,851,244 | A | * | 11/1974 | Mounce .................. G01N 22/04 324/640 |
| 3,882,383 | A | * | 5/1975 | Matlin .................... G01R 17/10 324/696 |
| 3,916,678 | A | * | 11/1975 | Lohoff .................... G01N 33/246 73/73 |
| 4,052,666 | A | * | 10/1977 | Fletcher ................... G01N 22/00 324/643 |
| 4,484,133 | A | * | 11/1984 | Riggin .................... G01N 22/04 324/606 |
| 4,600,879 | A | * | 7/1986 | Scully .................... G01N 22/04 324/640 |
| 4,620,146 | A | * | 10/1986 | Ishikawa ................. G01N 22/04 324/634 |
| 4,674,325 | A | * | 6/1987 | Kiyobe ................... G01N 22/04 324/630 |
| 4,727,311 | A | * | 2/1988 | Walker .................... G01R 25/04 324/630 |
| 4,892,113 | A | * | 1/1990 | Fattahi ................... A01G 25/167 137/624.12 |
| 5,053,781 | A | * | 10/1991 | Milman ................... G01K 11/006 342/351 |
| 5,148,826 | A | * | 9/1992 | Bakhshaei ............. A01G 25/167 137/78.3 |
| 5,333,493 | A | * | 8/1994 | Cutmore ................. G01N 22/04 324/640 |
| 5,408,893 | A | * | 4/1995 | McLeroy ............... E21B 11/005 175/20 |
| 7,135,871 | B1 | * | 11/2006 | Pelletier ................. G01N 22/04 324/640 |
| 9,857,316 | B2 | | 1/2018 | Pratt et al. |
| 2011/0307177 | A1 | * | 12/2011 | Hong ...................... G01N 22/04 702/2 |
| 2013/0332115 | A1 | * | 12/2013 | Pratt ....................... G01N 22/04 702/190 |
| 2015/0181817 | A1 | * | 7/2015 | Runge .................... G08B 21/20 340/602 |
| 2015/0268218 | A1 | * | 9/2015 | Troxler ................... G01N 22/04 342/21 |
| 2018/0128925 | A1 | * | 5/2018 | Yunck .................... G01S 13/9023 |
| 2018/0224550 | A1 | * | 8/2018 | Guy ........................ G01S 7/025 |

FOREIGN PATENT DOCUMENTS

| | | | |
|---|---|---|---|
| CN | 101692128 | | 4/2010 |
| CN | 101738620 | | 6/2010 |
| CN | 101865909 | | 10/2010 |
| CN | 101900692 | | 12/2010 |
| CN | 101936921 | | 1/2011 |
| CN | 101949916 | | 1/2011 |
| CN | 201724913 | | 1/2011 |
| CN | 201754150 | | 3/2011 |
| CN | 102621163 | | 8/2012 |
| CN | 102735697 | | 10/2012 |
| CN | 103149220 | | 6/2013 |
| CN | 103336104 | | 10/2013 |
| CN | 103344653 | | 10/2013 |
| CN | 103969268 | | 8/2014 |
| CN | 104062654 | | 9/2014 |
| CN | 104267045 | | 1/2015 |
| CN | 104678078 | | 6/2015 |
| CN | 104678404 | | 6/2015 |
| CN | 204405567 | | 6/2015 |
| CN | 105352979 | | 2/2016 |
| CN | 105466957 | | 4/2016 |
| CN | 105606631 | | 5/2016 |
| CN | 105823516 | | 8/2016 |
| CN | 105893736 | | 8/2016 |
| CN | 106018439 | | 10/2016 |
| CN | 106125106 | | 11/2016 |
| CN | 106226260 | | 12/2016 |
| CN | 205879848 | | 1/2017 |
| CN | 106372434 | | 2/2017 |
| CN | 106483147 | | 3/2017 |
| CN | 106501186 | | 3/2017 |
| CN | 106569210 | | 4/2017 |
| CN | 106771089 | | 5/2017 |
| CN | 104677921 | | 6/2017 |
| CN | 107389895 | | 11/2017 |
| CN | 107424076 | | 12/2017 |
| CN | 107451522 | | 12/2017 |
| CN | 107862255 | | 3/2018 |
| CN | 108268735 | | 7/2018 |
| CN | 108535338 | | 9/2018 |
| CN | 105204024 | | 11/2018 |
| EP | 3097754 | | 11/2016 |
| KR | 20110017617 | | 2/2011 |
| KR | 20150091721 | | 8/2015 |
| RU | 2621876 | | 6/2017 |
| RU | 2016104019 | * | 8/2017 ............ A01G 25/09 |
| RU | 2631896 | | 9/2017 |
| RU | 2641715 | | 1/2018 |
| SU | 1402911 | | 6/1988 |
| WO | 201301129 | | 1/2013 |

OTHER PUBLICATIONS

Lakhankar et al, Applications of microwave remote sensing of soil moisture for agricultural applications, International Journal of Terraspace Science and Engineering, 2009, 11 pages (Year: 2009).*

Mladenova et al, Remote monitoring of soil moisture using passive microwave-basedtechniques—Theoretical basis and overview of selected algorithmsfor AMSR-E, Elsevier, 2014, 17 page (Year: 2014).*

* cited by examiner

SYSTEM AND METHOD TO DETECT GROUND MOISTURE

BACKGROUND OF THE INVENTION

1. Field of Invention

The present invention relates generally to ground moisture detection and in particular to a system and method for measuring microwave emissivity using passive microwave radiometers to produce a soil moisture profile.

2. Description of Related Art

In the field of agriculture, it is well known that crops require water, provided either naturally by precipitation or by irrigation methods. Crop fields have variability in soil type, topography and nutrient levels, with varying moisture levels over a widespread area, as well as throughout the soil depth through to the root zone. Soil moisture is an important parameter in agriculture and providing the ideal amount of irrigation dependent on soil moisture improves overall results. Typically, farmers either guess the soil moisture or use stationary in-situ moisture probes. Both of these methods give unreliable results, which can lead to yield loss due to over or under irrigation practices.

Many farmers endeavor to practice precision agriculture, where the use of technology allows optimization of crop growth. One aspect of precision agriculture is to adjust irrigation and fertilizer application according to the needs of the soil and of the crop.

It is commonly known that there is a correlation between ground microwave emissivity and soil water content. Thus, microwave sensors may be used to determine the level of moisture within the soil, such as for agricultural purposes.

Typically, active microwave sensors (RADAR) are used to detect soil moisture, whereby the active sensor transmits electromagnetic energy towards the terrain then receives and records the reflected energy. Passive microwave sensors measure the level of microwave emissions emitted naturally by the soil without reflecting a generated signal therefrom. Existing systems measure a single frequency to determine soil moisture, providing a moisture reading down to a specific soil depth. They do not provide information about the distribution of soil moisture along the soil profile. Current microwave soil moisture sensors are either bulky, heavy or expensive.

SUMMARY OF THE INVENTION

According to a first embodiment of the present invention there is disclosed a system for measuring moisture in soil below the ground surface comprising at least one passive microwave sensor device configured to measure natural thermal emissions from the soil and output a data signal and a processing circuit operably coupled to the at least one passive microwave sensor wherein the processing circuit is configured to receive the data signal and compile a soil moisture profile. The system further comprises a wide-band antenna wherein the at least one passive microwave sensor is located therein and an elongate horizontal mounting frame extending between first and second ends wherein the first end is securable to a mobile agricultural device and wherein the wide-band antenna is secured to the second end so as to position the wide-band antenna at a distance above the ground surface.

The wide-band antenna may be configured to direct the natural thermal emissions to the at least one passive microwave sensor device. The at least one passive microwave sensor device may comprise a plurality of passive microwave sensor devices. The wide-band antenna may be selected from a group consisting of a cavity-backed antenna, a microstrip patch antenna or a log-periodic antenna.

The mounting frame may include a bend located between the first and second ends so as to angle the wide-band antenna relative to the ground surface. The bend may be formed at an angle selected to be between 30 and 60 degrees. The natural thermal emissions may be comprised of microwave emissivity signals.

The at least one microwave sensor device may be configured to simultaneously measure a plurality of microwave emissivity signals. The plurality of microwave emissivity signals may be selected from between a 400 MHz emissivity signal and an 800 MHz emissivity signal.

The mobile agricultural device may comprise a mobile irrigation system frame. The mobile agricultural device may be selected from a group consisting of a tractor, a combine or a sprayer.

The processing circuit may include a GPS receiver operable to output position data corresponding to the soil moisture profile. The processing circuit may be configured to compile the position data and the soil moisture profile to output a soil moisture map.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
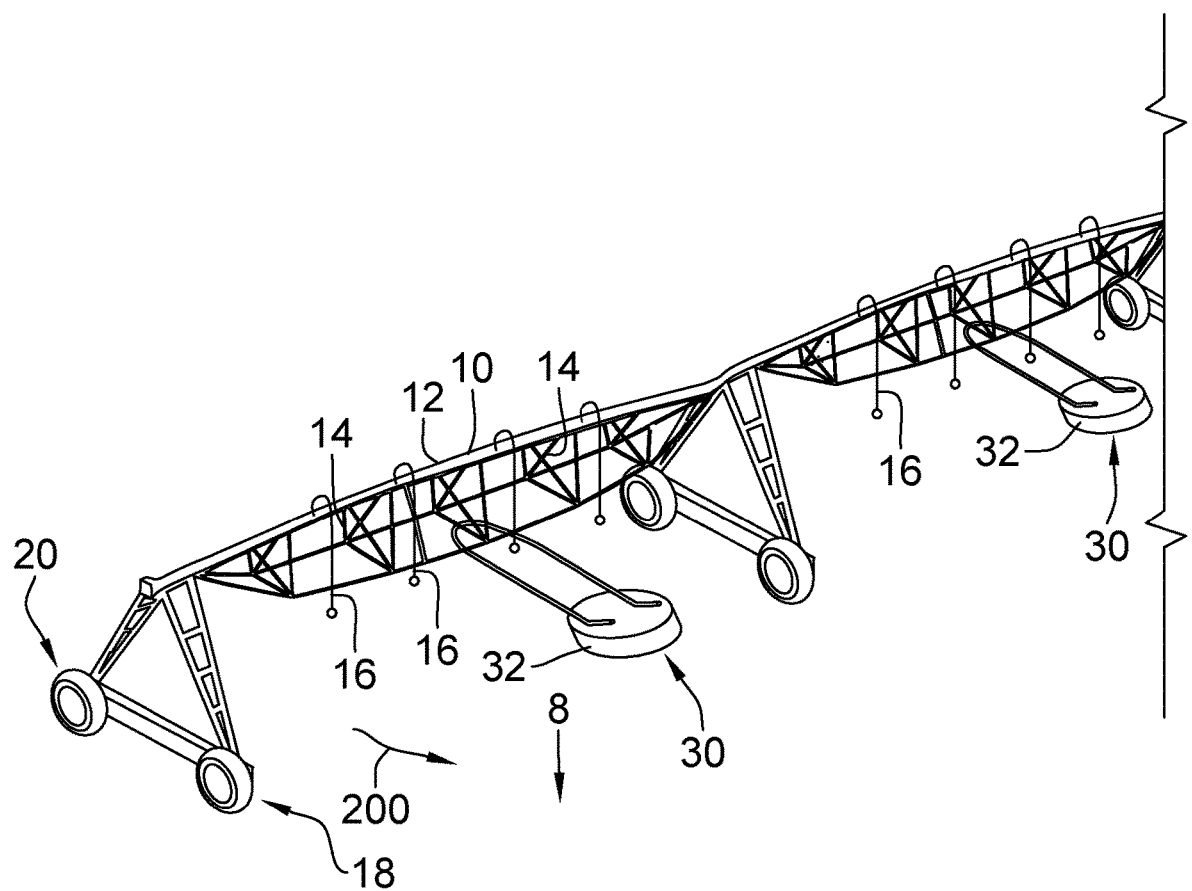
FIG. 1 is a perspective view of a mobile irrigation system frame having a plurality of ground moisture detection systems mounted thereon according to a first embodiment of the present invention.

Referring to FIG. 1, a system for detecting ground moisture according to a first embodiment of the invention is shown generally at 30, secured to a mobile irrigation system 10, as is commonly known. The system 30 includes a sensor assembly 32 operable to measure microwave emissions from the soil 8 to determine a soil moisture profile, as will be set out further below.

The mobile irrigation system 10 includes a central conduit 12 supported by a plurality of trusses 14, as are commonly known. A plurality of fluid emitting devices 16 extend from the central conduit 12. The irrigation system 10 moves in a direction indicated generally at 200 such that the irrigation system 10 has leading and trailing edges, 18 and 20 respectively. With the irrigation system 10 in operation, the ground area forward of the leading edge 18 has not yet been irrigated while the ground area behind the trailing edge 20 has been irrigated. Each system 30 is mounted to a truss 14 on the irrigation system 10 such that the sensor assembly 32 is positioned proximate to the leading edge 18, to measure the soil moisture profile ahead of the irrigated area. Each system may be positioned above the soil by a height of at least 39 inches (1 m) although it will be appreciated that for different antenna types, other distances may be useful as well.

Figure 2:
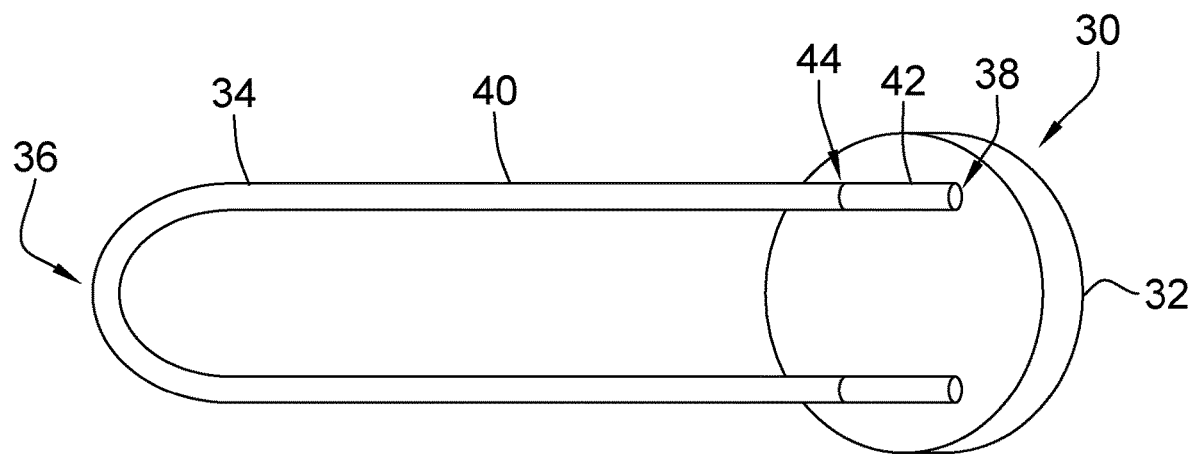
FIG. 2 is a top view of the ground moisture detection system of FIG. 1.
Figure 3:
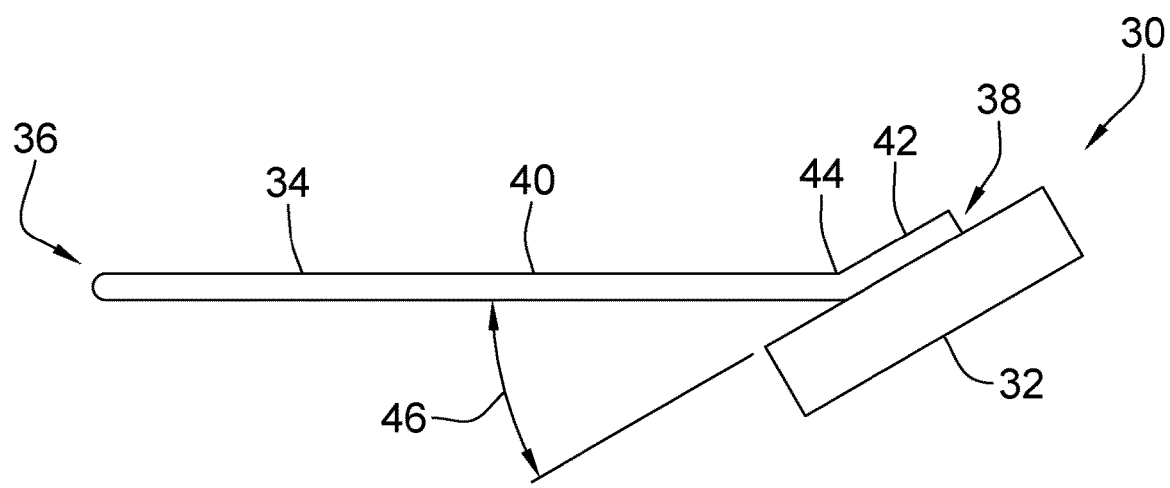
FIG. 3 is a side view of the ground moisture detection system of FIG. 1.

Turning now to FIGS. 2 and 3, the system 30 includes a mounting frame 34 extending between first and second ends, 36 and 38, respectively. A horizontal portion 40 extends from the first end 36 and an angled portion 42 extends from the second end 38 with a bend 44 therebetween. The bend 44 is selected to produce an angle 46 of between 30 and 60 degrees from horizontal between the horizontal portion 40 and the angled portion 42. Although the mounting frame 34 is illustrated as an elongate member bent into a U-shape, it will be appreciated that other frames may be used as well. The sensor assembly 32 is secured to the second end 38 at the angled portion 42 such that the sensor assembly 32 is angled relative to the ground 8, as illustrated in FIG. 1.

Figure 4:
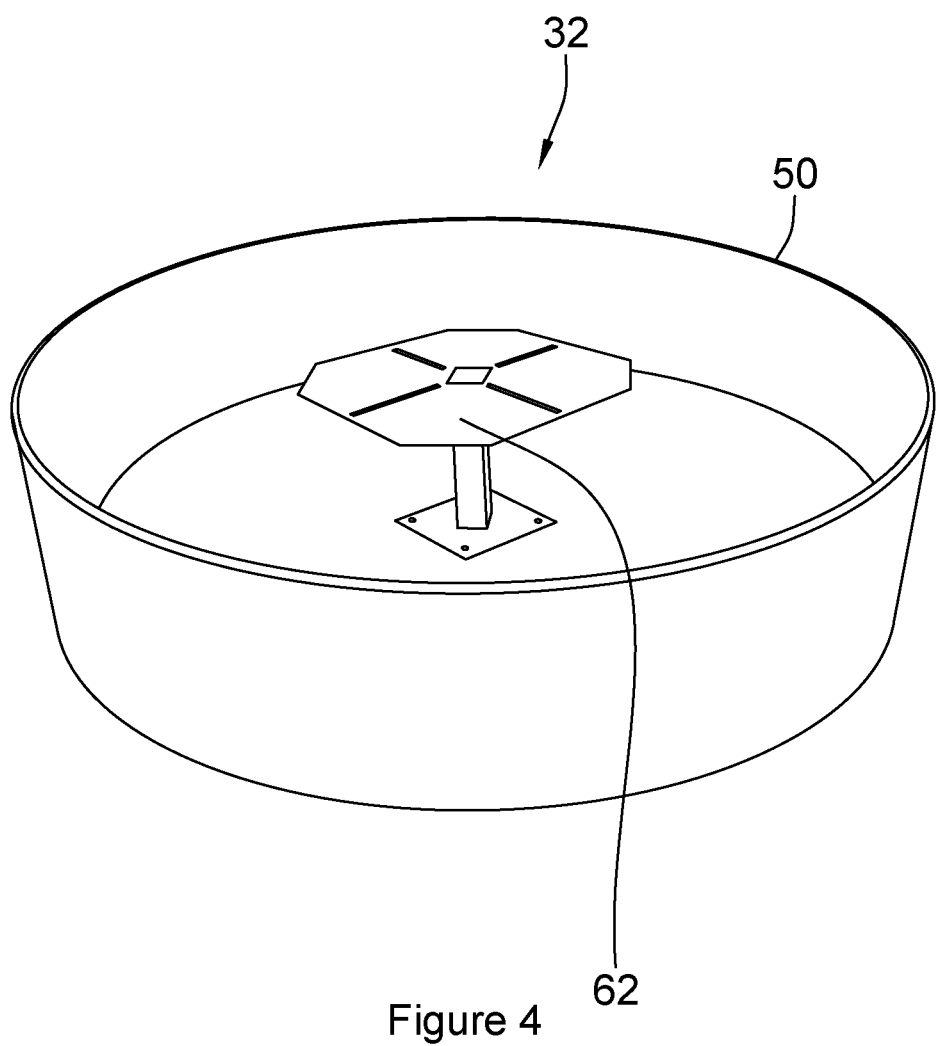
FIG. 4 is a perspective view of the sensor assembly.

Referring now to FIG. 4, the sensor assembly 32 is comprised of a control system 60 associated with and connected to a wide-band antenna (WB antenna) 62. The WB antenna 62 is illustrated as a cavity backed antenna with a 60 degree half-power beamwidth over the frequency of 400 to 800 MHz, any antenna providing horizontal and linear polarization, wide frequency bandwidth and a half-power beamwidth of not more than 65 degrees may be used such as, by way of non-limiting example, a cylindrical antenna, a microstrip patch antenna, a log-periodic antenna or any other suitable antenna. Each WB antenna 62 may also include a reflector 50 therearound as are commonly known. The control system 60 may be mounted behind the WB antenna 62 or may optionally be remote therefrom. The antenna may also be selected to be a dual polarized antenna such as, by way of non-limiting example, having horizontal and vertical hands.

Each WB antenna 62 is configured to measure a plurality of microwave frequency emissivity levels, such as, by way of non-limiting example, between 400 MHz and 800 MHz. It will be appreciated that these two frequencies translate to measurements at approximately 75 cm and 40 cm soil depth. The microwave frequency emissivity levels can be selected as desired, dependent on the desired soil depth measurement levels. Based on the measurement of emissivity at two or more different frequencies, the distribution of soil moisture along the profile can be estimated. For example, if soil moisture increases at high depths, the emissivity at 400 MHz will be lower than the emissivity at 800 MHz. If soil moister decreases at higher depths, the emissivity at 400 MHz will be higher than the emissivity at 800 MHz. If the soil moisture does not change along the profile, microwave emissivity will be nearly equal at 400 and 800 MHz. It will be appreciated that different frequencies may also be selected to measure the moisture at different depths as is practicable such as, by way of non-limiting example, up to 3 GHz. The ability to measure the soil moisture at a plurality of depths enables the creation of a profile of soil moisture within the ground which can be further utilized to provide advanced information about the soil type, density and performance.

Figure 6:
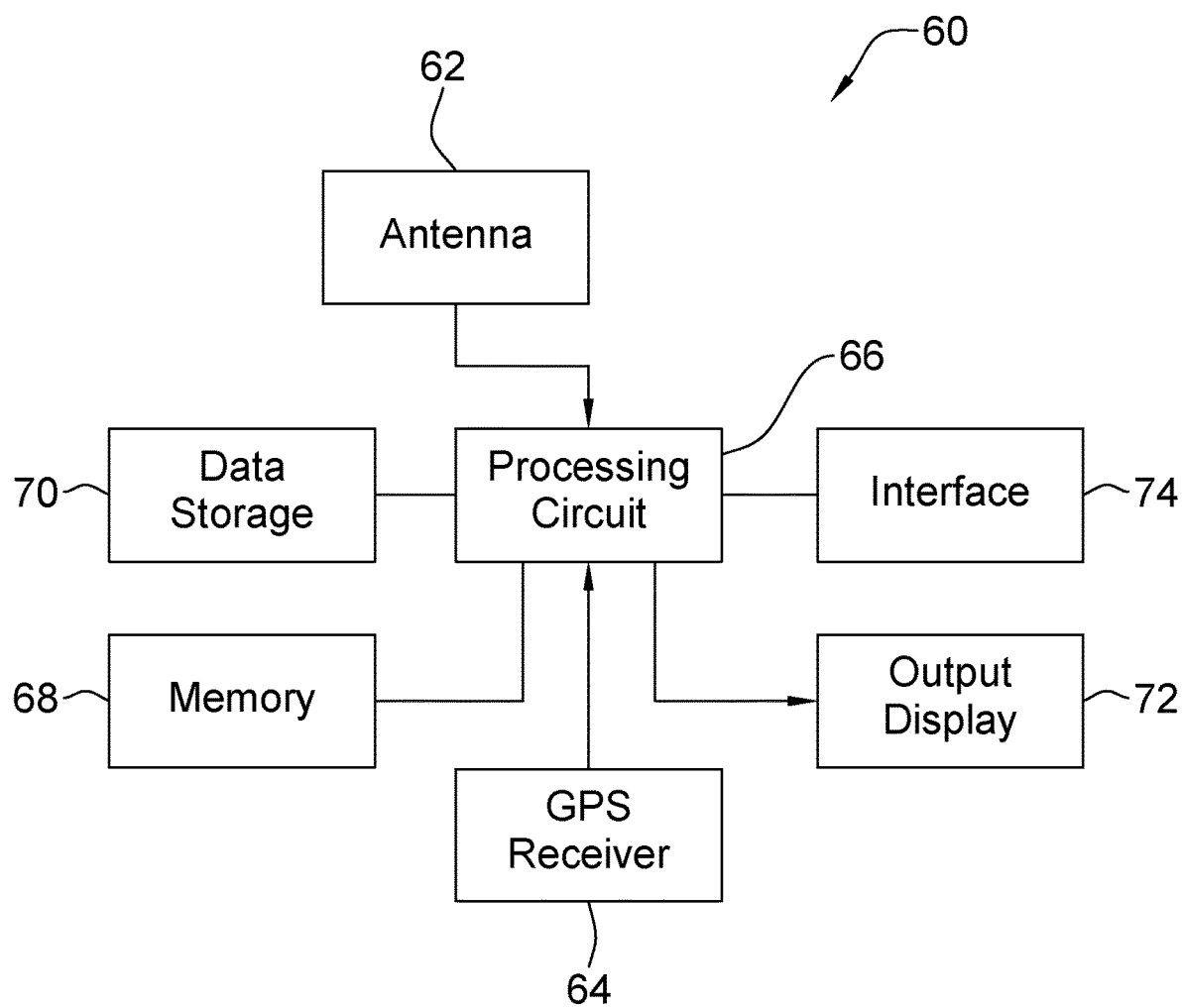
FIG. 6 is a schematic diagram of the ground moisture detection system.

Turning now to FIG. 6, as set out above, each sensor assembly 32 includes a control system 60. The WB antennas 62 receive microwave emissions from the soil, as set out above, and output a data signal. Simultaneously, a GPS receiver 64 receives signals from global positioning system satellites, as is commonly known, to determine the current position of the system 30. The control system 60 comprises a processing circuit 66 and memory 68 that stores machine instructions that, when executed by the processing circuit 66, cause the processing circuit 66 to perform one or more of the operations and methods described herein. The processing circuit 66 may optionally contain a cache memory unit for temporary local storage of instructions, data, or computer addresses. The control system 60 further includes a data storage 70 of any conventional type operable to store a plurality of entries containing the microwave emissivity and position information for a plurality of sensor and GPS receiver measurements and may optionally include an output display 72 for displaying the corresponding data results. The control system 60 also includes an interface 74 such as a radio transmitter, ethernet adapter, USB connection or the like for providing communication between the database manager and the processing circuit 66 and data storage 70.

More generally, in this specification, including the claims, the term "processing circuit" is intended to broadly encompass any type of device or combination of devices capable of performing the functions described herein, including (without limitation) other types of microprocessing circuits, microcontrollers, other integrated circuits, other types of circuits or combinations of circuits, logic gates or gate arrays, or programmable devices of any sort, for example, either alone or in combination with other such devices located at the same location or remotely from each other. Additional types of processing circuit(s) will be apparent to those ordinarily skilled in the art upon review of this specification, and substitution of any such other types of processing circuit(s) is considered not to depart from the scope of the present invention as defined by the claims appended hereto. In various embodiments, the processing circuit 66 can be implemented as a single-chip, multiple chips and/or other electrical components including one or more integrated circuits and printed circuit boards.

Computer code comprising instructions for the processing circuit(s) to carry out the various embodiments, aspects, features, etc. of the present disclosure may reside in the memory 68. In various embodiments, the processing circuit 66 can be implemented as a single-chip, multiple chips and/or other electrical components including one or more integrated circuits and printed circuit boards. The processing circuit 66, together with a suitable operating system, may operate to execute instructions in the form of computer code and produce and use data. By way of example and not by way of limitation, the operating system may be Windows-based, Mac-based, or Unix or Linux-based, among other suitable operating systems. Operating systems are generally well known and will not be described in further detail here.

Memory 68 may include various tangible, non-transitory computer-readable media including Read-Only Memory (ROM) and/or Random-Access Memory (RAM). As is well known in the art, ROM acts to transfer data and instructions uni-directionally to the processing circuit 66, and RAM is used typically to transfer data and instructions in a bi-directional manner. In the various embodiments disclosed herein, RAM includes computer program instructions that when executed by the processing circuit 66 cause the processing circuit 66 to execute the program instructions. More generally, the term "memory" as used herein encompasses one or more storage mediums and generally provides a place to store computer code (e.g., software and/or firmware) and data that are used by the control system 60. It may comprise, for example, electronic, optical, magnetic, or any other storage or transmission device capable of providing the processing circuit 66 with program instructions. Memory 68 may further include a floppy disk, CD-ROM, DVD, magnetic disk, memory chip, ASIC, FPGA, EEPROM, EPROM, flash memory, optical media, or any other suitable memory from which processing circuit 66 can read instructions in computer programming languages.

Figure 5:
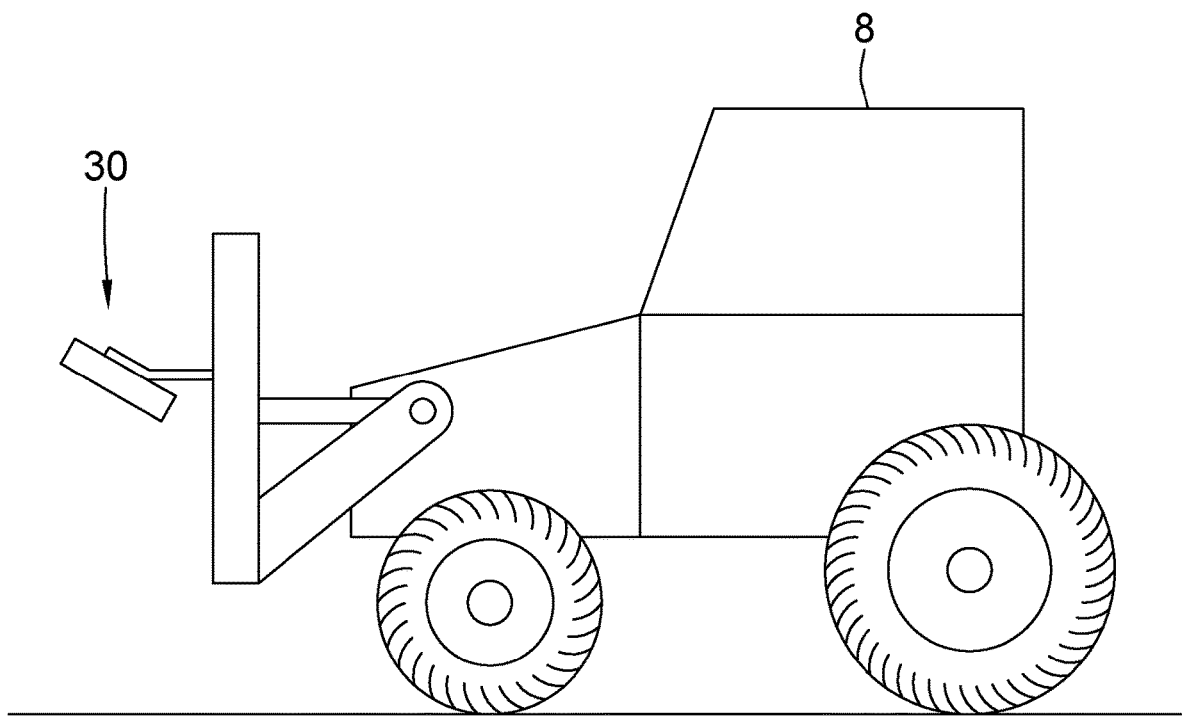
FIG. 5 is a side view of the ground moisture detection system mounted on a tractor.

Turning now to FIG. 5, the system 30 may be mounted to any mobile device, such as, by way of non-limiting example, a tractor 8, a combine, a sprayer or any other movable farming implement. This configuration is useful to collect soil moisture profiles for dryland farming crops, to determine adequate amounts of fertilizer application. As illustrated in FIG. 1, multiple sensor assemblies 32 may be mounted at different locations along such equipment such as, by way of non-limiting example a sprinkler.

While specific embodiments of the invention have been described and illustrated, such embodiments should be considered illustrative of the invention only and not as limiting the invention as construed in accordance with the accompanying claims.

What is claimed is:

1. A system for measuring moisture in soil below the ground surface comprising:
   at least one passive microwave sensor device configured to measure natural thermal emissions from the soil and output a data signal;
   a processing circuit operably coupled to said at least one passive microwave sensor wherein said processing circuit is configured to receive said data signal and compile a soil moisture profile;
   a wide-band antenna selected to measure two hands of polarization wherein said at least one passive microwave sensor is located therein; and
   an elongate horizontal mounting frame extending between first and second ends wherein said first end is securable to a mobile agricultural device and wherein said wide-band antenna is secured to said second end so as to position said wide-band antenna at a distance above the ground surface.

2. The system of claim 1 wherein said wide-band antenna is configured to direct said natural thermal emissions to said at least one passive microwave sensor device.

3. The system of claim 2 wherein said at least one passive microwave sensor device comprises a plurality of passive microwave sensor devices.

4. The system of claim 1 wherein said wide-band antenna is selected from a group consisting of a cavity-backed antenna, a microstrip patch antenna or a log-periodic antenna.

5. The system of claim 1 wherein said mounting frame includes a bend located between said first and second ends so as to angle said wide-band antenna relative to the ground surface.

6. The system of claim 5 wherein said bend is formed at an angle selected to be between 30 and 60 degrees.

7. The system of claim 1 wherein said natural thermal emissions are comprised of microwave emissivity signals.

8. The system of claim 7 wherein said at least one microwave sensor device is configured to simultaneously measure a range of microwave emissivity signals.

9. The system of claim 8 wherein said plurality of microwave emissivity signals are selected from between a 400 MHz emissivity signal and an 800 MHz emissivity signal.

10. The system of claim 1 wherein said two hands of polarization comprise horizontal and vertical hands.

11. The system of claim 1 wherein said mobile agricultural device comprises a mobile irrigation system frame.

12. The system of claim 1 wherein said mobile agricultural device is selected from a group consisting of a tractor, a combine or a sprayer.

13. The system of claim 1 wherein said processing circuit includes a GPS receiver operable to output position data corresponding to said soil moisture profile.

14. The system of claim 13 wherein said processing circuit is configured to compile said position data and said soil moisture profile to output a soil moisture map.

* * * * *